United States Patent
Suchan et al.

(10) Patent No.: US 8,177,099 B2
(45) Date of Patent: May 15, 2012

(54) CARTRIDGE

(75) Inventors: Matthias Suchan, Hachenburg (DE); Alexander Bublewitz, Herborn (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 589 days.

(21) Appl. No.: 11/514,572

(22) Filed: Sep. 1, 2006

(65) Prior Publication Data
US 2007/0051750 A1    Mar. 8, 2007

(30) Foreign Application Priority Data
Sep. 3, 2005    (DE) .......................... 10 2005 041 961

(51) Int. Cl.
*B67D 7/70*    (2010.01)

(52) U.S. Cl. ...................... 222/137; 222/145.6; 222/491; 604/90

(58) Field of Classification Search .................. 222/137, 222/145.1, 145.6, 491, 326, 327, 387, 495; 604/191, 218, 226, 232
See application file for complete search history.

(56) References Cited

U.S. PATENT DOCUMENTS

| | | | | |
|---|---|---|---|---|
| 3,941,128 A * | 3/1976 | Baldwin | .................. | 604/238 |
| 4,613,326 A * | 9/1986 | Szwarc | .................. | 604/89 |
| 4,690,306 A * | 9/1987 | Staheli | .................. | 222/80 |
| 4,735,616 A * | 4/1988 | Eibl et al. | .................. | 604/191 |
| 4,846,373 A * | 7/1989 | Penn et al. | .................. | 222/137 |
| 4,890,771 A * | 1/1990 | Morel et al. | .................. | 222/137 |
| 5,033,650 A * | 7/1991 | Colin et al. | .................. | 222/137 |
| 5,566,860 A * | 10/1996 | Schiltz et al. | .................. | 222/94 |
| 5,643,224 A * | 7/1997 | Szapiro et al. | .................. | 604/238 |
| 5,685,846 A * | 11/1997 | Michaels, Jr. | .................. | 604/90 |
| 6,311,869 B1 | 11/2001 | Hörth et al. | | |
| 6,331,173 B1 * | 12/2001 | Ljungquist | .................. | 604/191 |
| 6,547,101 B1 * | 4/2003 | Sogaro | .................. | 222/137 |
| 6,613,021 B2 | 9/2003 | Sogaro | | |
| 6,817,987 B2 | 11/2004 | Vetter et al. | | |
| 6,843,652 B2 * | 1/2005 | Xie et al. | .................. | 433/90 |
| 2003/0120217 A1 * | 6/2003 | Abergel | .................. | 604/191 |
| 2004/0104249 A1 * | 6/2004 | Horth et al. | .................. | 222/145.6 |
| 2005/0020984 A1 * | 1/2005 | Lesch, Jr. | .................. | 604/187 |
| 2007/0175921 A1 * | 8/2007 | Keller | .................. | 222/137 |

FOREIGN PATENT DOCUMENTS

| | | |
|---|---|---|
| DE | 100 38 882 | 4/2001 |
| DE | 201 07 507 | 4/2002 |
| DE | 101 40 704 | 3/2003 |
| EP | 1 426 017 | 6/2004 |
| WO | WO 2005/016170 | 2/2005 |

* cited by examiner

*Primary Examiner* — Kevin P Shaver
*Assistant Examiner* — Daniel R Shearer
(74) *Attorney, Agent, or Firm* — McDonnell Boehnen Hulbert & Berghoff LLP

(57) ABSTRACT

A cartridge for storing and dispensing substances that are in paste form and/or capable of flow is formed by at least one tube, in which a closure piston and a dispensing piston adjustable by means of a piston rod are disposed, so as to form a seal, in such a manner that a chamber is formed between the pistons. At least one passage opening is provided in the closure piston, and at least one projection is provided in the tube assigned to this closure piston and/or an outlet opening, whereby the passage opening and the projection are adapted to one another, in terms of their shape, in such a manner that the closure piston can be displaced between a closure position, in which the chamber is closed, and a dispensing position, in which the chamber stands in a flow connection with the outlet opening, by means of the passage opening.

1 Claim, 6 Drawing Sheets

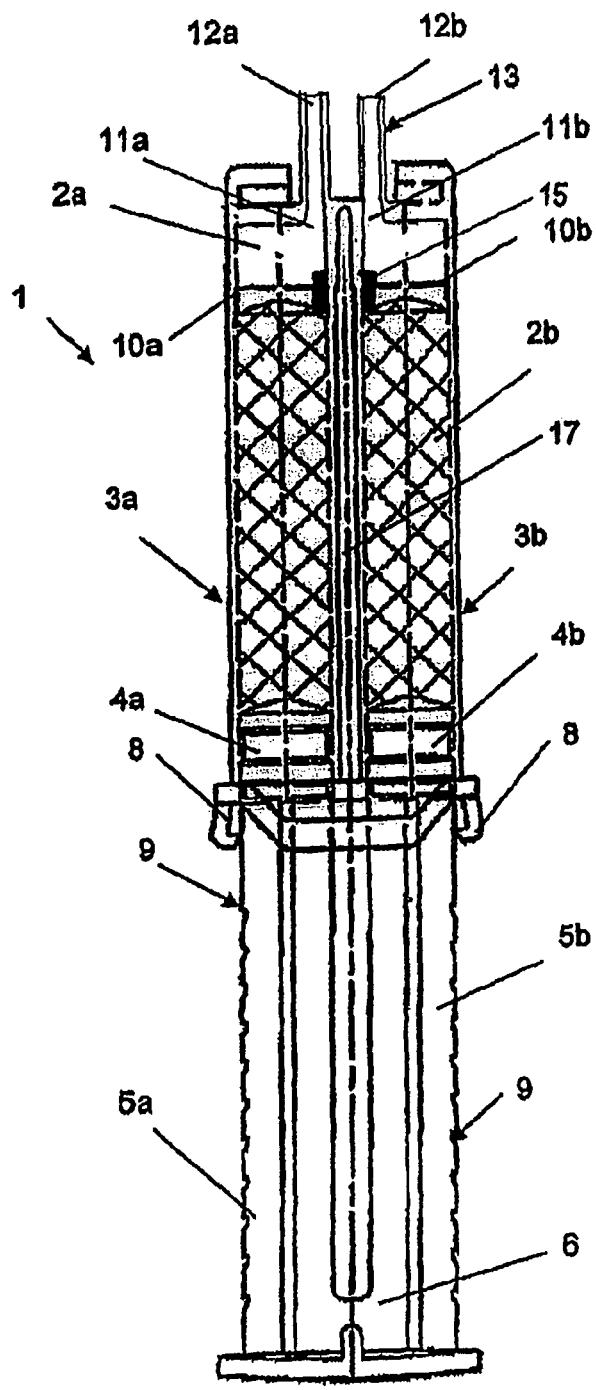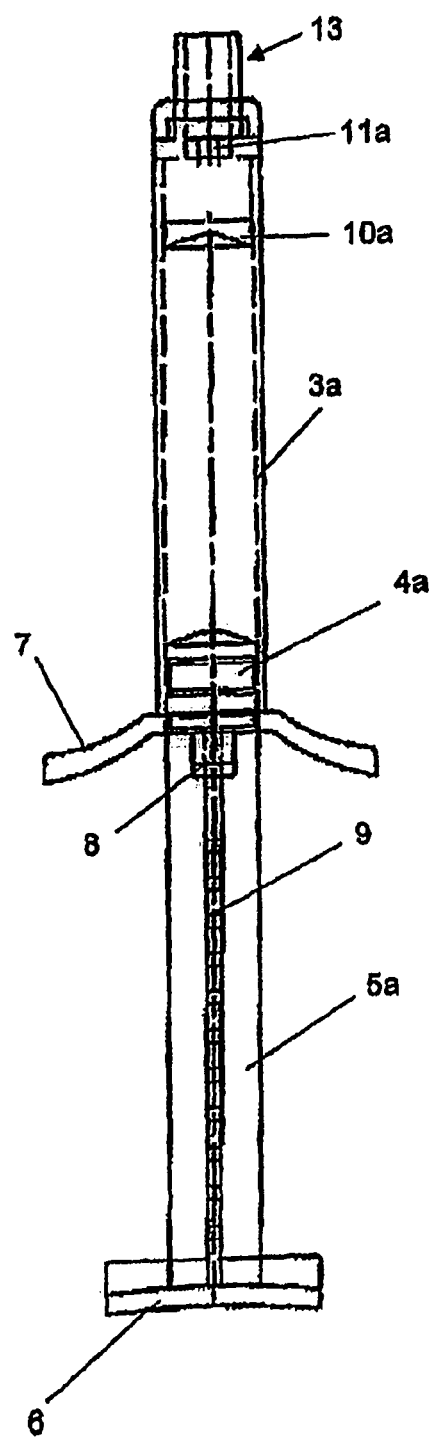

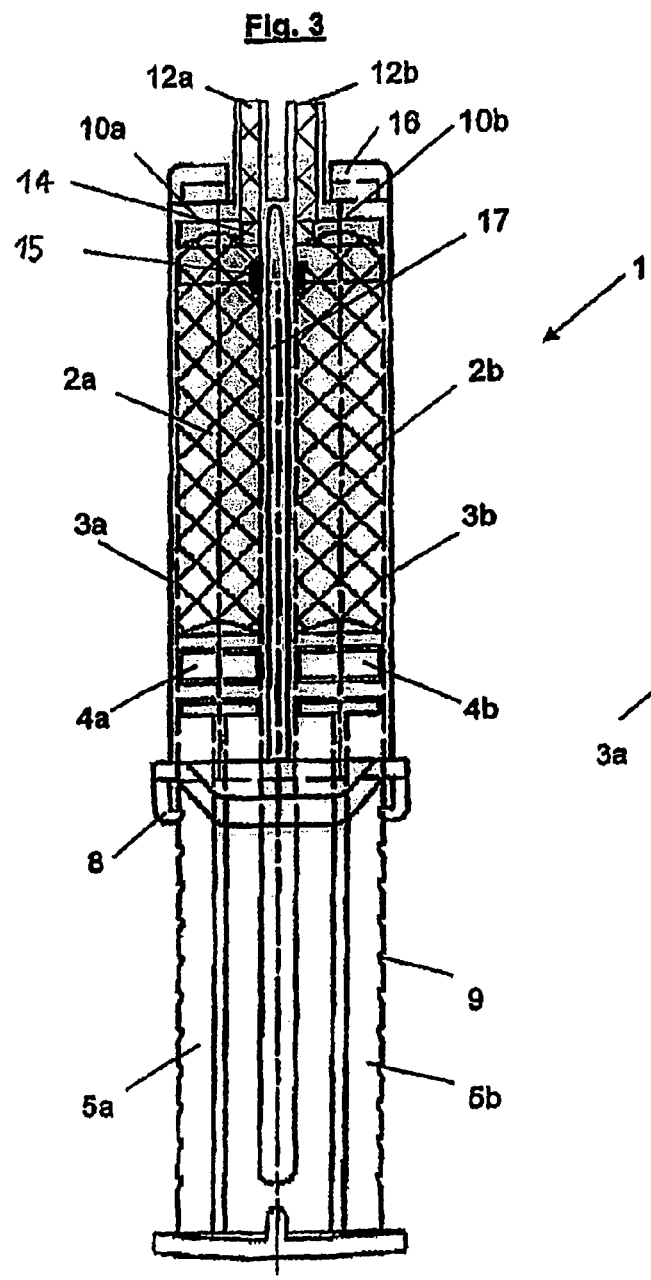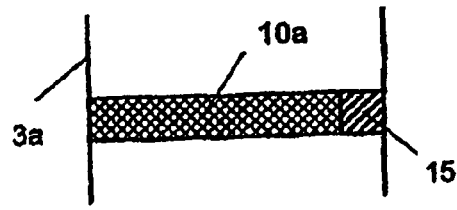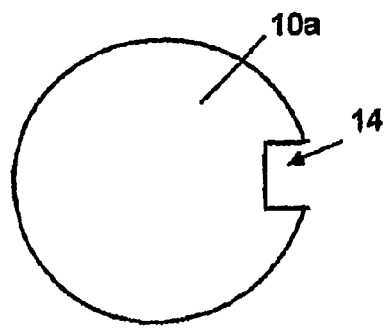

CARTRIDGE

CROSS REFERENCE TO RELATED APPLICATIONS

Applicants claim priority under 35 U.S.C. §119 of German Application No. 10 2005 041 961.5 filed Sep. 3, 2005.

BACKGROUND OF THE INVENTION

1. Field of the Invention

The present invention relates to a cartridge, particularly for storing and dispensing substances in paste form or capable of flow. The cartridge has at least one tube, for example a circular-cylinder tube, in which a closure piston and a dispensing piston adjustable by means of a piston rod are disposed, in each instance, so as to form a seal and to be displaceable, spaced apart from one another, in such a manner that a chamber for accommodating substances is formed between the dispensing piston and the closure piston. In this connection, an outlet opening is provided in each tube.

2. The Prior Art

Particularly in the dental sector, it is usual to store and transport materials in cartridges, from which these can be dispensed by way of a piston. Thus a dual cartridge is known from DE 100 38 882 A1, for example, in which two components for producing an impression mass are directly accommodated in the cartridges.

A dual cartridge structured in the manner of a syringe, in which two substances to be mixed with one another are accommodated in the chambers of this cartridge, which are oriented parallel to one another, is described in EP 1 426 017 A2. The two chambers have an opening at one end, in each instance, which are sealed by means of a closure part for transport and storage. To activate this dual cartridge, the closure part must be pressed into the chambers, so that a dispensing channel provided in the closure part is released. This method of procedure must be explained to a user before the first activation. Furthermore, this known dual cartridge can be used for only a single dose (unidose) and must be disposed of afterwards.

Alternatively to this cartridge, it is also known to package such materials in tubular bags, which can be introduced into the cartridges, which can then be used multiple times. On the one hand, it must be possible to seal such systems as hermetically as possible, for transport and storage, because the components can react with one another or with the surroundings or both. On the other hand, these systems must be easy for a user to open. For this purpose, the tubular bags must be pierced or cut open, without the components contaminating the reusable cartridges in this connection. In some application cases, this requirement has proven to be difficult.

Furthermore, a dual chamber syringe is proposed in DE 101 40 704 A1, in which a center plug, by means of which the dual chamber syringe is divided into two chambers, in which two components can be stored separated from one another, is provided, in addition to a dispensing plug. To apply these components, pressure is exerted on one of the components, by way of the dispensing plug, in such a manner that the center plug is pushed into a position in which it releases the bypass channel formed in the dual chamber syringe. In this open position, the center plug is locked in place by means of a projection on the inside of the syringe. The two substances can mix with one another, particularly if these substances are well-miscible liquids, and be dispensed jointly from the dual chamber syringe. Such dual chamber syringes, however, are also suitable only for one-time use, if the substances accommodated in the two chambers react with one another after mixing, and harden, for example. Furthermore, mixing of the two substances accommodated in the dual chamber syringe is perceived to require improvement, in some cases, particularly if these substances are not liquids.

A cartridge of the type stated initially is known from WO2005/016170 A2. Because the closure pistons of this known cartridge are freely movable in the tubes, they can slide out of their closure position during transport or storage. As a result, the substances accommodated in the cartridge can exit or react with one another or both. Penetration of germs into this known cartridge also cannot be optimally prevented.

SUMMARY OF THE INVENTION

In contrast to the above arrangements, it is an object of the present invention to provide a cartridge of the type stated initially, in which the substances can be stored so that they are sealed well with regard to one another and the surroundings, without making dispensing from the cartridge more difficult. At the same time, the cartridge should be particularly easy to open.

These and other objects are accomplished, according to the invention, substantially by providing the closure piston with at least one passage opening and the tube assigned to this closure piston and/or the outlet opening with at least one projection. In this connection, the passage opening and the projection are adapted to one another, in terms of their shape, so that the closure piston can be displaced between a closure position and a dispensing position. In the closure position, the chamber is closed. In the dispensing position, the chamber stands in a flow connection with the outlet opening, by means of the passage opening.

To dispense the substance from the cartridge, it is merely necessary to displace the dispensing piston by means of the piston rod, so that the closure piston is pushed into the dispensing position by means of the pressure that the substance accommodated in the chamber transfers from the dispensing piston. The cartridge can therefore be opened, i.e. activated intuitively by a user, without further explanations, in that pressure is exerted on the piston rod, as is usual in the case of syringes, for example. Removing or pressing in a closure plug, or piercing the packaging to open it, is therefore not required. At the same time, the cartridge according to the invention can be produced in cost-advantageous and simple manner, for example as an injection-molded part. In this connection, the cartridge can be used both for one-time doses and subsequent disposal of the complete cartridge (unidose), or for multiple doses (multidose), whereby a suitable application device can remain on the outlet opening after every use, which then serves as a closure.

The passage opening in the closure piston is preferably positioned in such a manner, according to the invention, that a substance can flow through the passage opening into the outlet opening essentially without being deflected. The flow resistance is clearly reduced by this arrangement in comparison with known solutions.

According to a preferred embodiment of the invention, a projection that does not extend over the full axial length of the tube is provided on the inside of each tube. In this embodiment, the closure piston of each tube has an outer contour adapted to the inner contour of the tube, with a passage opening, which can be laid against the projection, forming a seal. In the closure position, the chamber is therefore closed off by means of the passage opening that lies against the projection, forming a seal. After the closure piston has been displaced, however, the passage opening, which is no longer in contact with the projection, makes it possible to dispense a substance out of the chamber, through the passage opening in the closure piston.

Alternatively, the outlet opening can have a channel that is cylindrical at least in certain regions, on the inside of which channel a projection is provided, whereby the closure piston has an outer contour adapted to the inner contour of the channel, with a passage opening, which can be laid against the projection, forming a seal. Consequently, the closure piston is disposed in the outlet opening of the tube, at least in certain regions. More specifically, the closure piston, in the closure position, is disposed at least essentially in the tube, closing off the outlet openings, and in the dispensing position, is disposed at least essentially in the outlet nozzle, releasing the outlet openings. In this connection, the closure piston can have the shape of a circular ring or a segment of a circular ring.

According to another embodiment of the invention, the cartridge is configured with two tubes disposed parallel to one another, in which a dispensing piston is disposed in displaceable manner, in each instance. The outlet openings of the tubes open into a common outlet nozzle. On the inside of the common outlet nozzle, at least one projection that does not extend over the full axial length of the outlet nozzle is provided. The closure piston has an outer contour adapted to the inner contour of the outlet nozzle, with at least one passage opening, which can be laid against the projection, forming a seal. In this embodiment, the closure piston is therefore not disposed on the cylindrical part of the tubes, for example, but rather is disposed in the outlet nozzle of the tubes, both in its closure position and in its dispensing position.

In order to prevent tilting of the closure piston, it is preferred if the closure piston rests against the inner wall of the tube, or of the outlet opening or the outlet nozzle, respectively, along the greatest possible circumference region. For this purpose, the passage opening preferably takes up less than 50% of the inner circumference of the tube, or of the outlet opening or outlet nozzle, respectively. On the other hand, the passage opening is also supposed to be large enough so that a sufficient amount of the substance can be dispensed from the chamber, without an unnecessary increase in the flow resistance. This capability can be achieved if the passage opening of the closure piston, which forms a channel for passage of the substances that are capable of flow or in paste form or both, is larger than approximately 5%, for example, of the inner cross-sectional area of the tube, or of the outlet opening or the outlet nozzle, respectively, as a function of the viscosity of the substance.

Two tubes, particularly tubes disposed coaxially one inside the other, which open into a common outlet nozzle that forms the outlet openings, may be provided. If so, it is preferred that a common closure piston having at least one passage opening is provided in the outlet nozzle. The common closure piston blocks a flow connection between the chambers and the common outlet opening in its closure position. The closure piston can then be configured in ring shape, for example.

In a further development of this idea of the invention, the inner one of the two tubes may have an outlet segment having at least one radial opening. The outlet segment projects into the outlet nozzle, the end of which, facing away from the dispensing piston, is closed off. The closure piston can then be configured as a ring-like disk that can be displaced in the outlet nozzle, so as to form a seal, the passage opening of which can be displaced on the outlet segment, forming a seal. As an alternative to this arrangement, it is also possible that the inner one of the two tubes has an outlet segment that projects into the outlet nozzle, the end of which, facing away from the dispensing piston, is open. In this connection, the closure piston is configured as a disk that can be displaced in the outlet nozzle, forming a seal, which disk has a recess that can be laid against the outlet segment, forming a seal, and/or a projection that can be introduced into the outlet segment, forming a seal. In the case of these embodiments, the closure piston can be introduced into the outlet nozzle as a closure only after the chambers have been filled with the substances, if necessary.

In order to prevent the closure piston from twisting in the tube, the outlet opening and/or the outlet nozzle, particularly when it is being inserted, and thereby causing the passage opening to be not precisely aligned relative to the corresponding projection, an anti-twisting device that interacts with the closure piston can be provided. This anti-twisting device can be achieved, for example, by having the projection—with the exception of a region in the vicinity of the outlet opening—extend over the entire axial length of the tube. In addition, passage openings are provided in both pistons, with which the pistons are guided on the projection, to prevent twisting. Alternatively to this arrangement, noses or similar projections could also be provided on the pistons, with which the pistons are guided in groove-like recesses in the inner wall of the tube, to prevent twisting. Also possible is an anti-twisting device by means of an inner contour of the tube that is not circular in cross-section, and a corresponding outer contour of the pistons.

If a finger grip and/or an accommodation for a dispensing device is provided on at least one tube, the cartridge according to the invention can be activated manually, similar to a syringe, or can be emptied mechanically, by means of a dispensing device.

If the channels have different lengths and/or different volumes, these channels can be adapted to the different viscosities or running properties of the substances. In this way, it can be prevented, for example, that one substance exits from the outlet nozzle before the other one. As a consequence, the mixing result is already optimal at the start of the dispensing process.

Preferably, dose markings and/or means for releasable fixation of the dispensing piston in the closure position are provided on at least one tube and/or on at least one piston rod. The dose markings can be configured by means of engagement noses and notches, for example, so that the user has an optical, acoustical and/or tactile monitoring possibility. Thus, the two piston rods can form a common dual piston rod with a central engagement rod, to which an engagement nose provided between the tubes is assigned. In this manner, dispensing a predetermined amount of the substances from the cartridge is facilitated. In this connection, the dual piston rod, according to a preferred embodiment, has engagement elements on only one side, whereby engagement noses are disposed between the tubes also on only one side. In this way, with the essentially mirror-symmetry structure of the dual piston rod, it is possible either to introduce the dual piston rod between the tubes so that the engagement elements and the engagement noses enter into contact with one another, or to avoid engagement via insertion of the dual piston rod turned by 180° about the longitudinal axis.

The means for releasable fixation of the dispensing piston in the closure position can be formed by means of an engagement, a change in cross-section within the tube, or the like, in order to prevent the piston rods, i.e. the dispensing piston from being activated unintentionally during transport or storage. Alternatively, it is also possible to fix the dispensing piston or the piston rods in place by way of a predetermined breaking point, which is cut open upon activation of the cartridge.

A mixer and/or an application device can be provided at the outlet nozzle of the cartridge according to the invention. These devices can either be configured in one piece with the outlet nozzle, or be releasably attached to it. When this cartridge is used for multiple doses (multidose), the mixer or the application device can remain on the cartridge after use, in each instance. In this way the components that have been mixed together with one another are caused to harden in the mixer, for example. The hardened mixture therefore forms a closure for the cartridge after the first activation. For renewed use, the old mixer or similar device must be removed and replaced with a new one.

In a further development of this idea of the invention, at least one closure piston may be accommodated in the mixer or the application device or both in its dispensing position, at least in certain regions. In this connection, the closure piston is pushed out of the cartridge, when the dispensing piston is activated, from its closure position in the cartridge, at least in part, and can actually be accommodated entirely in the mixer or similar device in its dispensing position, if necessary. Thus, construction space for storage of the closure piston is saved in the cartridge.

As an alternative to configuring the projection on the inner wall of the tube, this projection can also be provided on a front face, in the dispensing direction, of a rod that projects into the tube from the rear. In this connection, the projection is structured as a broadened head region of the rod, for example, whereby the size of the passage opening corresponds approximately to that of the head region of the rod.

According to another embodiment of the invention, a cartridge having at least two tubes is provided, which form a chamber, in each instance, whereby the chamber walls have a different permeability, particularly a different air permeability. This feature can be achieved either by means of different material properties of the chamber walls, or by sealing one of the chambers, particularly with regard to the surroundings, by means of a tubular bag accommodated in it, for example. On the one hand, the different permeability of the chambers can lower the production costs of a cartridge, if particular sealing requirements are set for only one chamber. On the other hand, the different permeability of the chambers can also permit an air exchange or the like with the surroundings, which might be desirable in some cases.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In this connection, all of the characteristics that are described and/or shown in the drawings represent embodiments of the invention, in themselves or in any desired combination, independent of how they are combined in the claims or their antecedents.

In the drawings, wherein similar reference characters denote similar elements throughout the several views:

FIG. 1 is a sectional view of a dual cartridge according to a first embodiment of the invention, in its delivery position or closed position;

FIG. 2 is a side view, the dual cartridge according to FIG. 1;

FIG. 3 shows the dual cartridge according to FIG. 1 in the activated dispensing position;

FIG. 4a is a sectional view of a detail of a cartridge according to FIG. 1;

FIG. 4b is a top view of the closure piston according to FIG. 4a;

FIG. 5 is a sectional view of a detail of a cartridge according to a second embodiment of the invention, in its closed position;

FIG. 6 is a sectional view of the cartridge according to FIG. 5 in its activated dispensing position;

FIG. 7 is a view into the outlet nozzle of the cartridge according to FIG. 5;

FIG. 8 is a sectional view of a cartridge according to a third embodiment of the invention, in its activated dispensing position;

FIG. 9 is in a sectional view of a detail of a cartridge according to FIG. 1;

FIG. 10 is in a top view of the closure piston according to FIG. 9;

Figure 11:
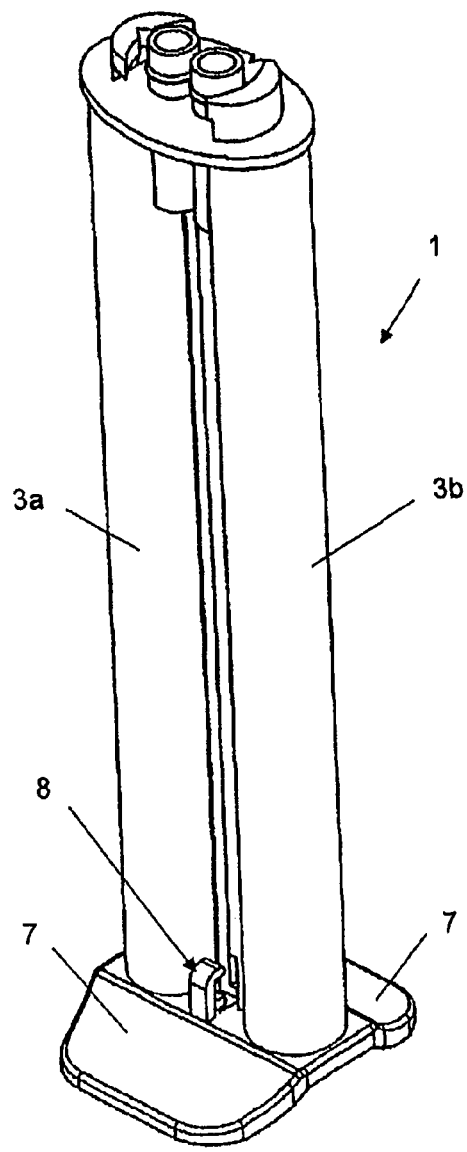
Figure 12:
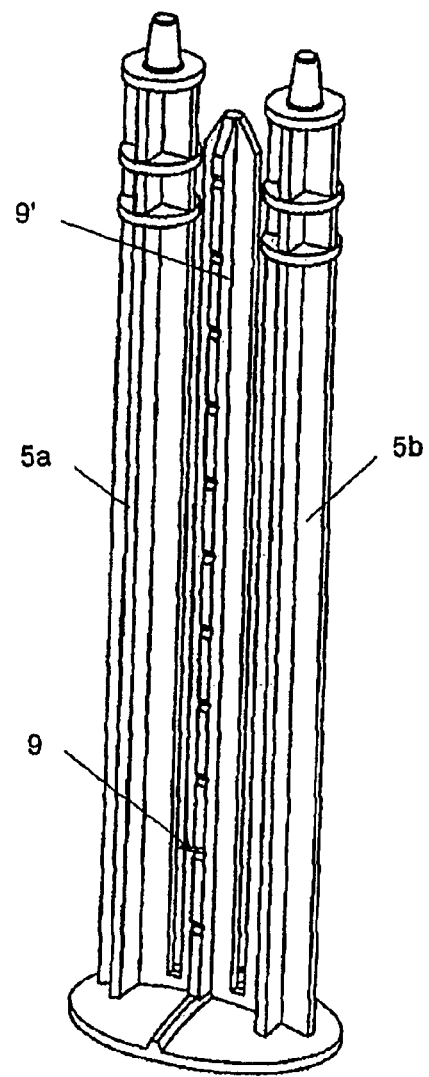
Figure 13:
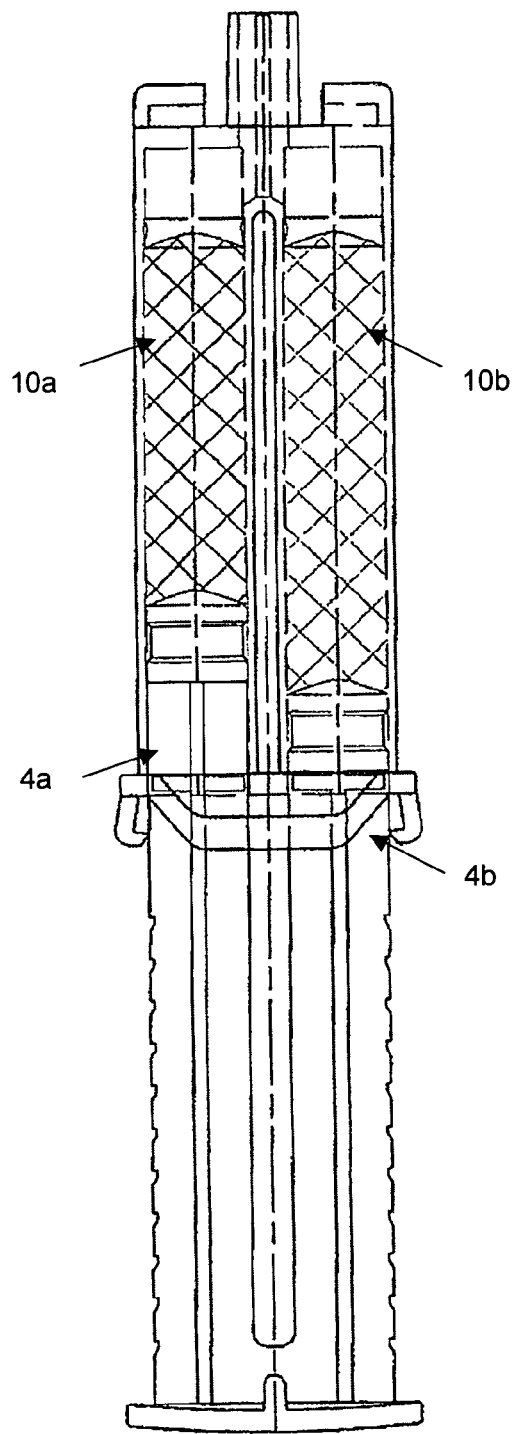
Figure 14:
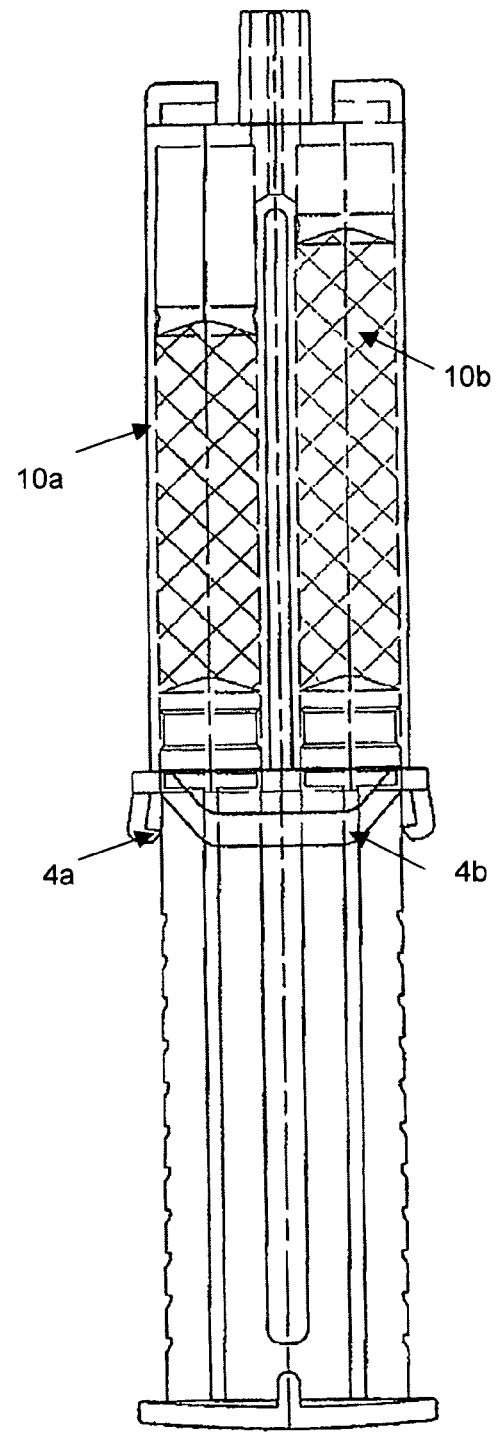

FIG. 11 is a perspective view of a dual cartridge according to another embodiment of the invention, FIG. 12 is a perspective view of a piston rod arrangement for the dual cartridge according to FIG. 11; and FIGS. 13 and 14 are sectional views of a dual cartridge according to the first embodiment of the invention shown in FIG. 1, in its delivery position or closed position, with the closure pistons or dispensing pistons disposed offset relative to one another in an axial direction of the tubes.

DETAILED DESCRIPTION OF PREFERRED EMBODIMENTS

Referring now in detail to the drawings, the dual cartridge 1 shown in FIGS. 1 to 3 is formed by two cartridges 2a, 2b that are connected with one another in one piece. Each of these cartridges 2a, 2b consists of a tube 3a or 3b, respectively, which is closed off at the upper end, in the drawings, and is open on the opposite side.

In tubes 3a, 3b, a dispensing piston 4a, 4b is provided, in each instance, which closes off the open end of the tubes, forming a seal, and can be displaced in tubes 3a and 3b, respectively, by means of a piston rod 5a, 5b. In this connection, the two piston rods 5a, 5b are connected with one another, in one piece, by way of a common crosspiece 6, so that dispensing pistons 4a and 4b, which are fixed in place on the piston rods, can be activated at the same time.

As is evident from FIG. 2, finger grips 7 are provided at one end of tubes 3a, 3b, so that dual cartridge 1 can be activated in the manner of a syringe. Furthermore, engagement noses 8 are provided at the ends of tubes 3a, 3b, which come into engagement with engagement notches 9 on piston rods 5a, 5b when dispensing pistons are pushed into tubes 3a, 3b by means of piston rods 5a, 5b. In this connection, engagement noses 8 and engagement notches 9 are configured in such a manner that the engagements are easy to overcome manually, in order to obtain acoustical or tactile feed-back, for example, if dispensing pistons 4a, 4b have been displaced by a defined amount within tubes 3a, 3b. Engagement noses 8 and engagement notches 9 consequently serve for precise metering.

Furthermore, a closure piston 10a, 10b is accommodated in each of tubes 3a, 3b, in each instance, in displaceable manner and forming a seal, so that chambers are formed between closure pistons 10a, 10b and the dispensing pistons 4a, 4b, in each instance. In this connection, the closure pistons 10a, 10b shown in detail in FIGS. 4a and 4b are shown in their closure position in FIGS. 1 and 2, while closure pistons 10a, 10b have been displaced into their dispensing position in FIG. 3.

An outlet opening 11a, 11b is provided in the face wall of tubes 3a, 3b, in each instance, from which a channel 12a, 12b branches off, in each instance, which opens into an outlet nozzle 13 of dual cartridge 1, so that channels 12a, 12b are guided separately from one another up to their ends. The two outlet nozzles 13 shown in FIGS. 1 and 3 therefore stand in connection with the chambers that are defined in each of tubes 3a, 3b between dispensing pistons 4a, 4b and closure pistons 10a, 10b, in the dispensing position, and in which chambers a substance in paste form, for example, can be stored. Alternatively to this arrangement, a common outlet nozzle 13 can be provided, in which both channels 12a, 12b are guided.

As shown in detail in FIGS. 4a and 4b, closure pistons 10a, 10b have a passage opening 14, in each instance. Furthermore, a projection 15 is provided on the inner wall of tubes 3a, 3b, in each instance, the shape and size of which is adapted to passage opening 14, so that the edge of passage opening 14 lies against projection 15, forming a seal, in the closure position. Thus, closure pistons 10a, 10b close off the chamber, forming a seal, in their closure position.

If pressure is exerted on dispensing pistons 4a, 4b in the closure positions shown in FIGS. 1 and 2, by way of the piston rods 5a, 5b, this pressure is transferred to closure pistons 10a, 10b by means of the substances accommodated in the chambers, so that these pistons are displaced in an upward direction, in the drawings. In this connection, closure pistons 10a, 10b come loose from projections 15, so that a substance can flow out of the chamber, through the released passage openings 14, into the outlet openings 11a, 11b. This state is shown in FIG. 3. The substances accommodated in the chambers can therefore be dispensed from dual cartridge 1 through the outlet opening 11a, 11b and the channels 12a, 12b, by means of continued pressure on piston rods 5a, 5b. In this connection, the first opening or activation of dual cartridge 1 takes place intuitively, by means of activation as in the case of a conventional syringe.

A mixing tube sleeve, for example, can be set onto the outlet nozzle(s) 13, which sleeve forms a static mixer together with a mixing helix accommodated within it. Alternatively to this arrangement, a driven dynamic mixer or another suitable application device can also be attached to the face end of dual cartridge 1 and/or outlet nozzle 13. For this purpose, suitable attachment or locking means 16, for example a bayonet closure, a thread, or similar device, can be provided on the face of dual cartridge 1.

In the embodiment of dual cartridge 1 shown in FIGS. 1 to 3, channels 12a, 12b run to the end of outlet nozzles 13, proceeding from the outlet openings 11a, 11b in the face wall. Alternatively to this arrangement, it is also possible to have channels 12a, 12b run in the center wall 17, which connects the two cartridges 2a, 2b with one another, or rotated by 90° about the central axis of the dual cartridge 1, so that the channels lie behind one another in the plane of the drawing.

If only one common outlet nozzle 13 is provided for both channels, center wall 17 can extend so far into outlet nozzle 13 that channels 12a, 12b are guided separate from one another up to their ends. In this connection, the inlet nozzles of a mixer or similar device, not shown, can advantageously be inserted into the channels 12a, 12b of outlet nozzle(s) 13, or vice versa.

FIGS. 13 and 14 show the dual cartridge 1 shown in FIG. 1, including dispensing piston 4a, 4b and closure pistons 10a, 10b disposed offset relative to one another in an axial direction of the tubes, in the closure position.

Figure 5:
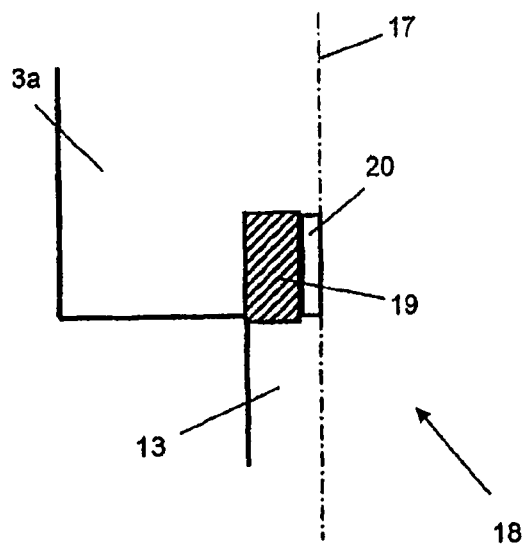
Figure 6:
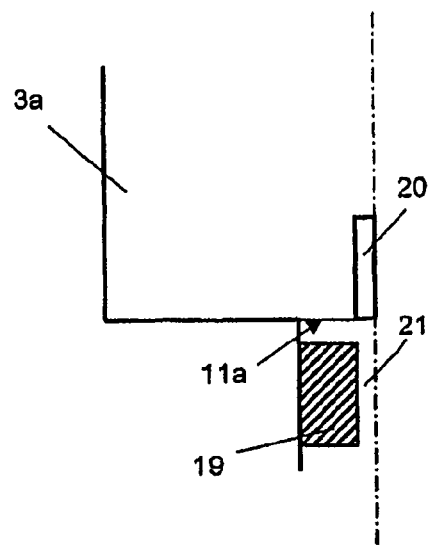
Figure 7:
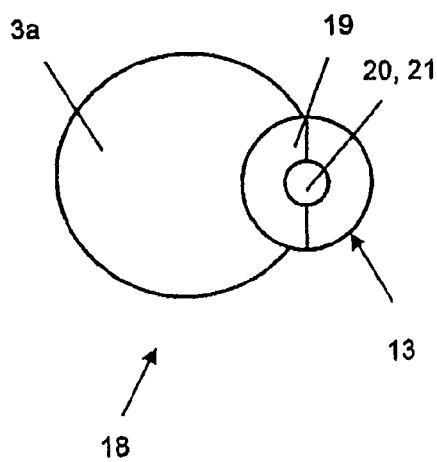

In FIGS. 5 to 7, another embodiment of a cartridge 18 according to the invention, which fundamentally has a similar structure as the dual cartridge described above, is shown, in detail. In this connection, only one tube 3a is shown in FIGS. 5 and 6, which opens into an outlet nozzle 13 by way of an outlet opening 11a.

As shown in FIG. 7, a closure piston 19 is assigned to tube 3a, which has a half-ring-shaped contour in cross-section. In the closure position of the closure piston 19 shown in FIG. 5, this piston is disposed on a projection 20 of center wall 17 of cartridge 18, in displaceable manner. In this connection, closure piston 19 is in tube 3a and closes off outlet opening 11a, and/or is pushed into this opening in certain regions, respectively. A substance accommodated in tube 3a consequently can not flow into outlet nozzle 13. If pressure is now exerted on the substance accommodated in tube 3a, closure piston 19 is pushed into outlet nozzle 13, as shown in FIG. 6, whereby the outer contour of closure piston 19 is adapted to the inner contour of outlet nozzle 13 in such a manner that closure piston 19 is guided to be easily displaceable in outlet nozzle 13. The passage bore 21 of closure piston 19, which serves for guidance on the projection 20, forms a channel, in the dispensing position, through which a substance can flow out of tube 3a through outlet opening 11a into outlet nozzle 13.

In FIG. 7, only one half-ring-shaped closure piston 19 for tube 3a is shown. If cartridge 18 is configured as a dual cartridge having two tubes, a second closure piston having essentially the same structure can be provided in the second tube, or in outlet nozzle 13, respectively. However, it is also possible to bring two closure pistons 19 together into a single circular-ring-shaped closure piston, which seals off both tubes and is displaced into outlet nozzle 13 when the substances are dispensed from the tubes of cartridge 18.

Figure 8:
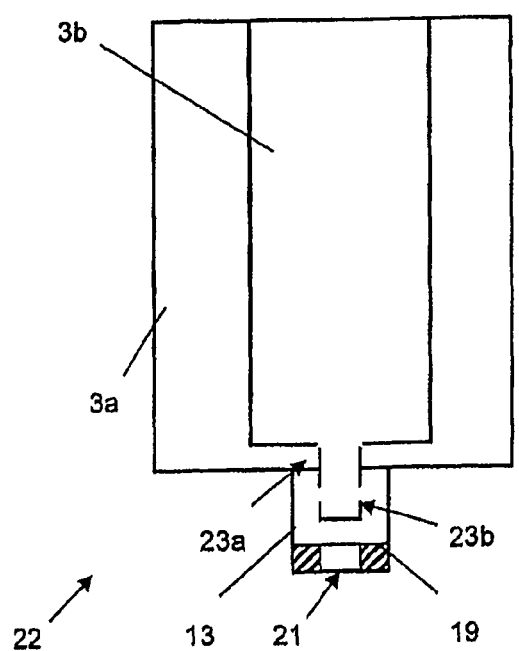

Another embodiment of a cartridge according to the invention is shown in FIG. 8. In this connection, rather than being disposed next to one another, the two tubes 3a, 3b are disposed concentrically inside one another. The outer tube 3a is provided with an outlet nozzle 13, whereby a first outlet opening 23a is formed between outlet nozzle 13 and tube 3a. A projection projects from inner tube 3b, through first outlet opening 23a, into outlet nozzle 13. A second, radial outlet opening 23b is formed in this projection of inner tube 3b.

A closure piston 19 configured as a circular-ring disk has a passage bore 21, the size of which is adapted to that of the projection of inner tube 3b. Closure piston 19 can therefore be disposed on the projection, closing off outlet openings 23a and 23b. When cartridge 22 is activated, closure piston 19 is displaced into the position shown in FIG. 8, whereby the substances accommodated in tubes 3a and 3b can flow through outlet openings 23a and 23b and through passage bore 21 of closure piston 19 into outlet nozzle 13.

Figure 9:
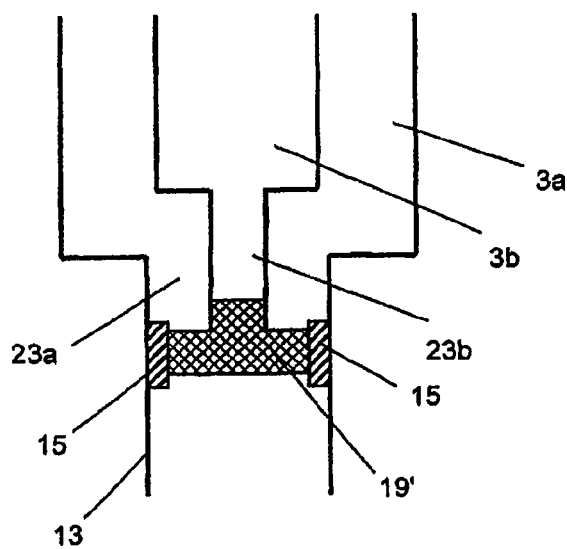
Figure 10:
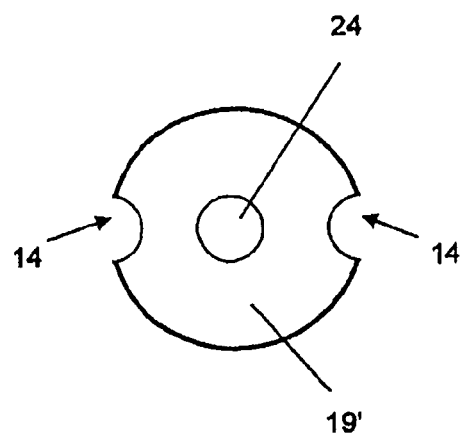

In the case of the embodiment shown in FIGS. 9 and 10, the two tubes 3a, 3b of the cartridge are also disposed concentrically inside one another. Fundamentally, more than the two tubes shown can also be provided in a cartridge, in this manner. The structure of the cartridge shown in this embodiment differs from the exemplary embodiment described above in that second outlet opening 23b of inner tube 3b is provided not radially but axially. Furthermore, two projections 15 are provided in outlet nozzle 13, on the inside.

The closure piston 19' accordingly has two passage openings 14, which are adapted to projections 15 in such a manner that passage openings 14 rest against the projections, forming a seal, in the closure position shown in FIG. 9. At the same time, a projection 24 is formed on the closure piston 19', which engages into second outlet opening 23b, forming a seal, and closes this opening off. Alternatively, a depression can also be formed in closure piston 19', which surrounds outlet opening 23b, forming a seal.

If pressure is now exerted on the substances contained in the chambers, by way of the dispensing pistons, not shown, closure piston 19' in the drawing is displaced downward, into its dispensing position, in which projections 15 no longer engage into passage openings 14. The substances can therefore exit from outlet nozzle 13, through passage openings 14. If necessary, closure piston 19' can be pushed entirely or partially out of outlet nozzle 13 of the cartridge, and be accommodated at least partially in a mixer or similar device connected with the cartridge, in its dispensing position.

In FIGS. 11 and 12, a further embodiment of a dual cartridge 1 having two tubes 3a, 3b connected with one another, as well as a piston rod arrangement for it, is shown. The piston rod arrangement has two piston rods 5a, 5b connected with one another, and an engagement rod 9' formed in one piece with them, which is disposed between the two piston rods. Engagement rod 9' has a cross-shaped cross-section, which is disposed in a corresponding opening in the crosspiece region of the dual cartridge that lies between the finger grips 7. There, an engagement nose 8 is also provided, in such a manner that this nose interacts with engagement notches 9 on the engagement rod 9', as dose markings, in order to give a user optical, acoustical and/or tactile control over the dose amount.

Accordingly, although only a few embodiments of the present invention have been shown and described, it is to be understood that many changes and modifications may be made thereunto without departing from the spirit and scope of the invention as defined in the appended claims.

What is claimed is:

1. A cartridge comprising:
a. two tubes disposed parallel to one another, having a common outlet nozzle with an outlet opening;
b. a closure piston disposed in said outlet nozzle, said closure piston having at least one passage opening; and
c. in each of the tubes one dispensing piston, said dispensing pistons adjustable via a common dual piston rod;
wherein said closure piston and said dispensing pistons are respectively disposed to form a seal and to be displaceable and spaced apart from one another so as to form chambers between said dispensing pistons and said closure piston for accommodating substances in paste form or capable of flow, which substances intermix with each other downstream of said closure piston;
wherein said closure piston is displaceable in a direction towards said outlet opening by means of the pressure that said substances accommodated in said chambers transfer from the dispensing pistons,
wherein said closure piston is displaceable between a closure position wherein said chambers are closed and
a dispensing position wherein said chambers have a flow connection with said outlet opening via said passage opening; and wherein a mixing tube is settable onto the outlet nozzle.

* * * * *